United States Patent [19]

Eaton

[11] Patent Number: 5,413,582
[45] Date of Patent: May 9, 1995

[54] INFLATABLE TOURNIQUET CUFF AND METHOD OF MAKING SAME

[75] Inventor: Robert P. Eaton, Conifer, Colo.
[73] Assignee: Electromedics, Inc., Parker, Colo.
[21] Appl. No.: 147,140
[22] Filed: Nov. 3, 1993
[51] Int. Cl.[6] ............................................. A61B 17/00
[52] U.S. Cl. ..................................... 606/202; 128/686
[58] Field of Search ................................ 606/201–203; 128/677–686

[56] References Cited

U.S. PATENT DOCUMENTS

| | | | |
|---|---|---|---|
| 2,199,408 | 5/1940 | Liberte | 606/202 |
| 2,571,461 | 10/1951 | Livingston et al. | |
| 3,633,567 | 1/1972 | Sarnoff | |
| 3,670,735 | 6/1972 | Hazlewood | |
| 4,116,605 | 9/1978 | Burrell | |
| 4,382,766 | 5/1983 | Feuerherm | |
| 4,432,718 | 2/1984 | Wurzer | |
| 4,635,635 | 1/1987 | Robinette-Lehman | |
| 4,979,953 | 12/1990 | Spence | 606/202 |
| 5,193,549 | 3/1993 | Bellin et al. | |
| 5,201,758 | 4/1993 | Glover | 606/203 |

Primary Examiner—Stephen C. Pellegrino
Assistant Examiner—William W. Lewis
Attorney, Agent, or Firm—Gary M. Polumbus; Holland & Hart

[57] ABSTRACT

An inflatable tourniquet cuff includes an inflatable bladder having an outer layer with a predetermined thickness and an inner layer with a thickness that is less than the predetermined thickness of the outer layer. An opening in the bladder allows for the inflation and deflation of the bladder. A fastener system attached to the bladder releasably secures the bladder about a patient's limb so that the thin inner layer is positioned adjacent the patient's skin. The thin layer is relatively flexible in comparison to the thick outer layer and thus expands to a greater degree than the outer layer upon inflation of the bladder. A preferred method of manufacturing the cuff includes extruding two plastic ribbons of different thicknesses, forming openings at predetermined intervals along the thicker ribbon, pressing the ribbons together and sealing them along their side edges, cutting the combined ribbons into predetermined lengths, sealing the combined ribbons at their ends to form an inflatable bladder, hermetically sealing a hollow flange to the thicker ribbon in alignment with the opening, and attaching a fastener system to the bladder so that the bladder may be releasably secured about a patient's limb. Alternatively, the cuff may be extruded from a single plastic ribbon having both a thick wall and an opposing thin wall.

4 Claims, 4 Drawing Sheets

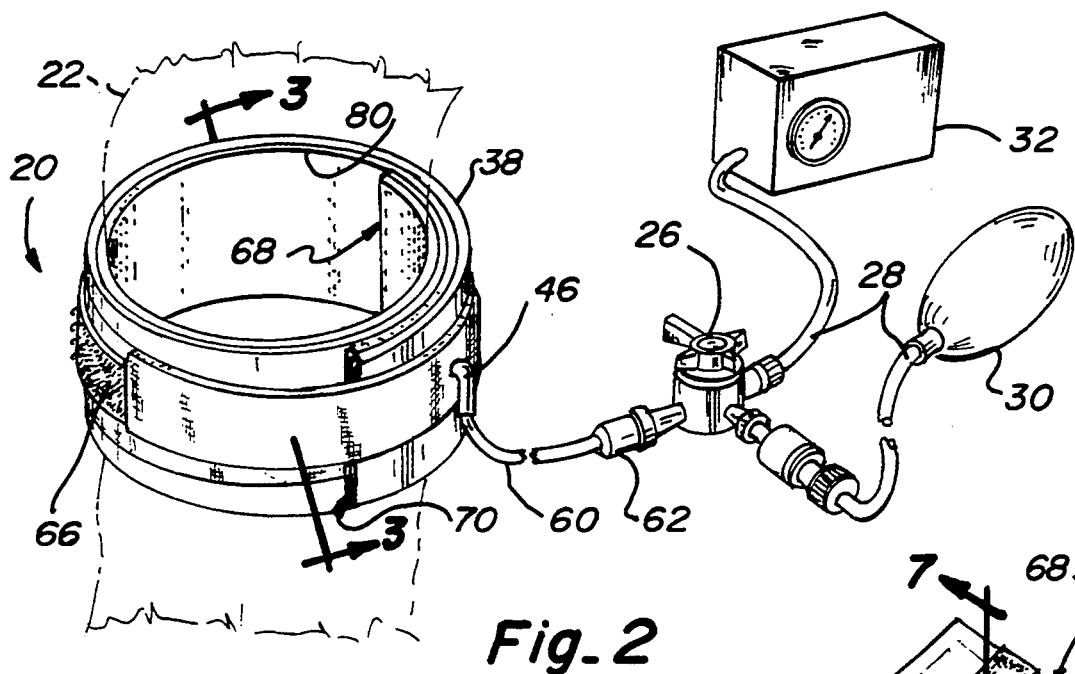
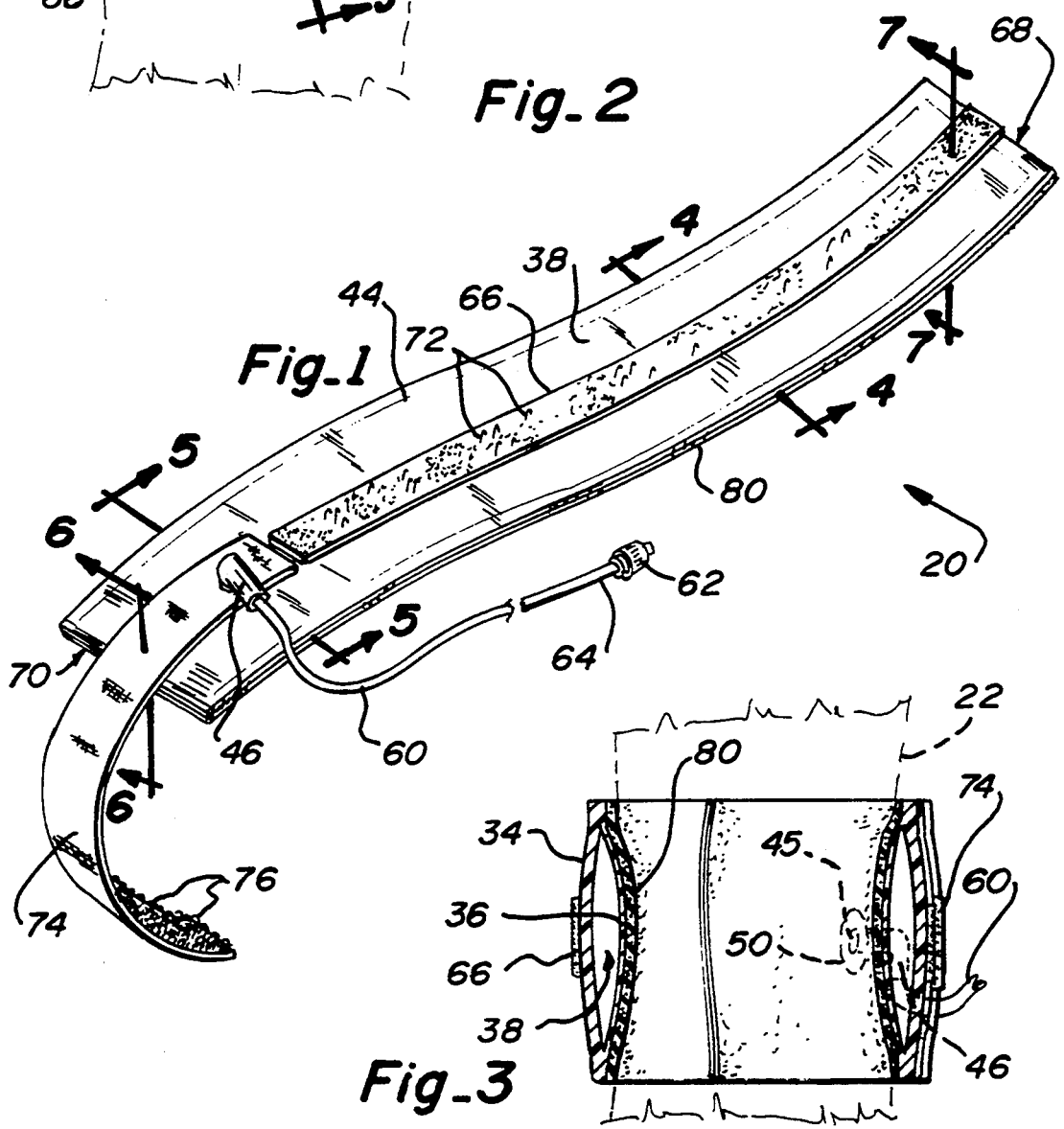

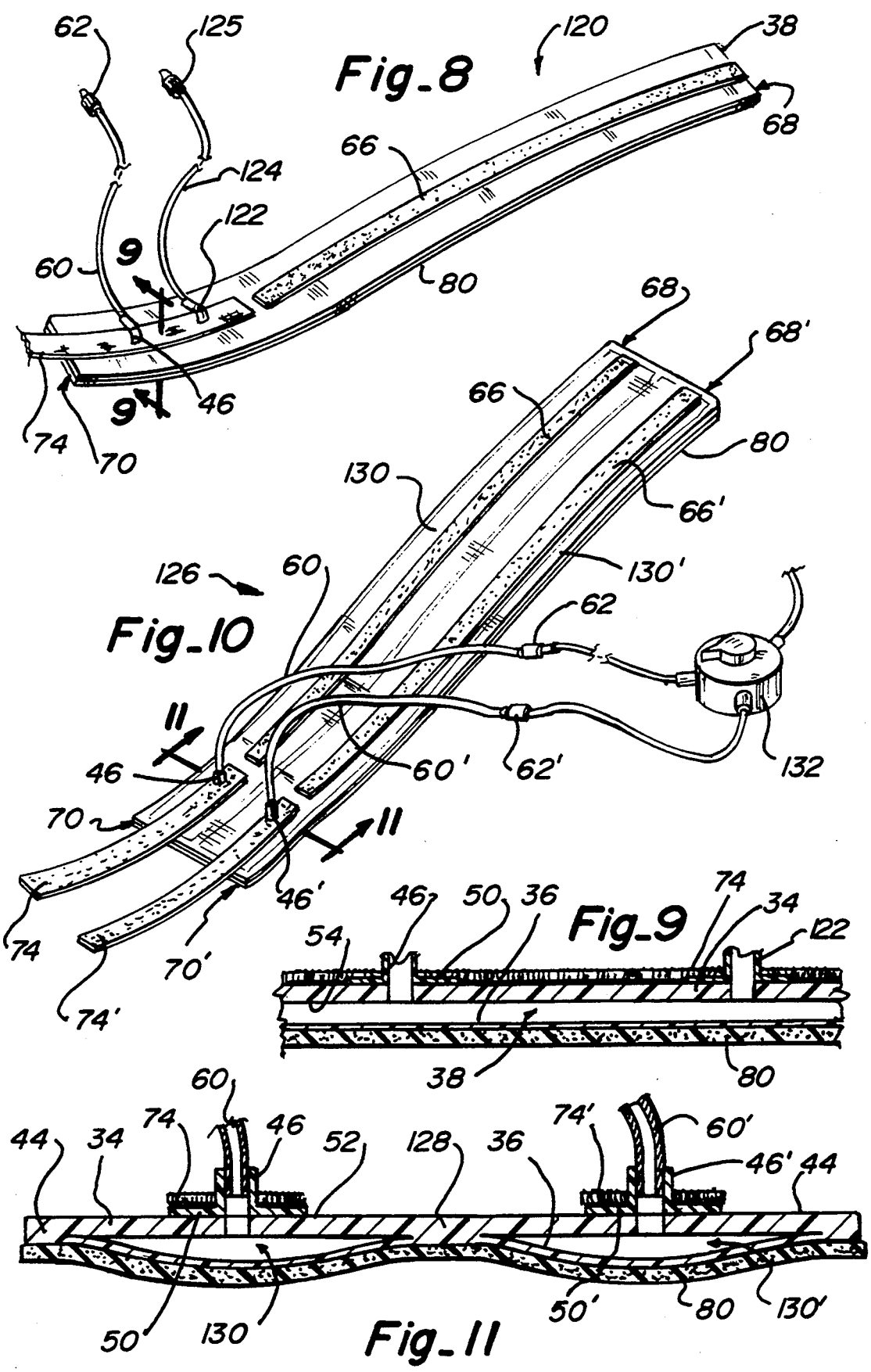

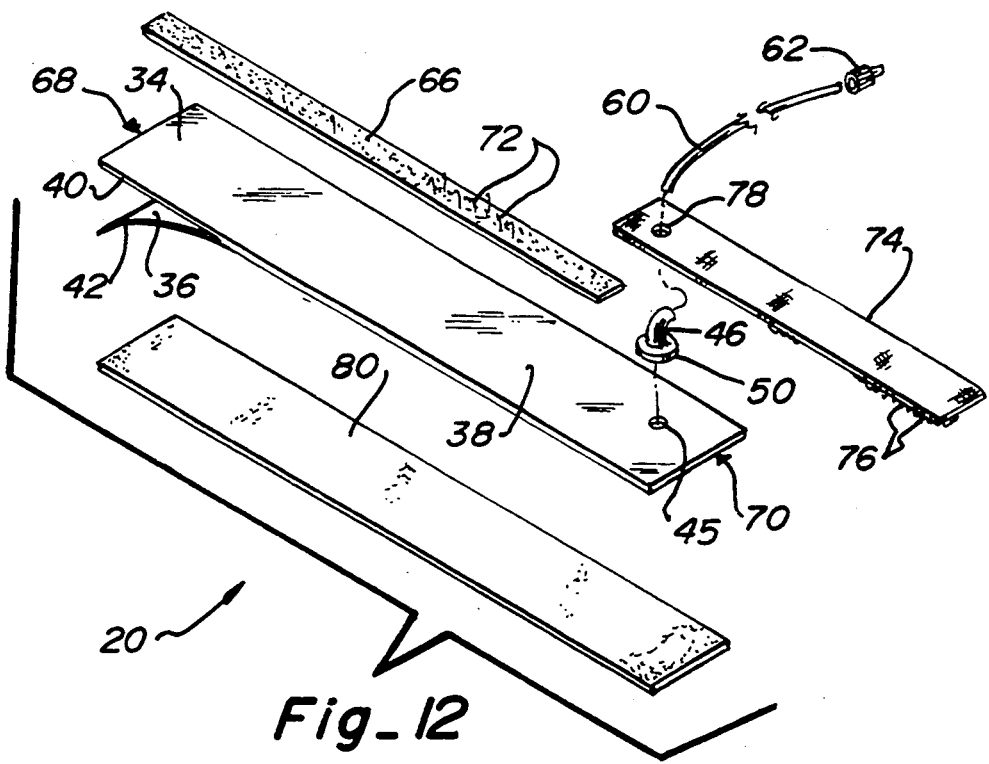
Fig_12
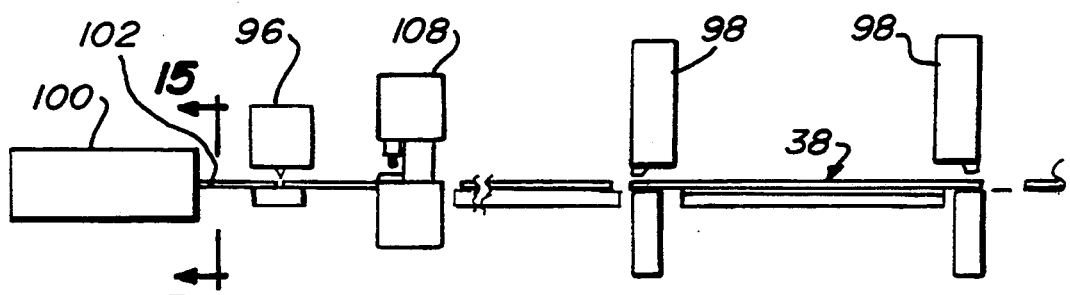
Fig_14
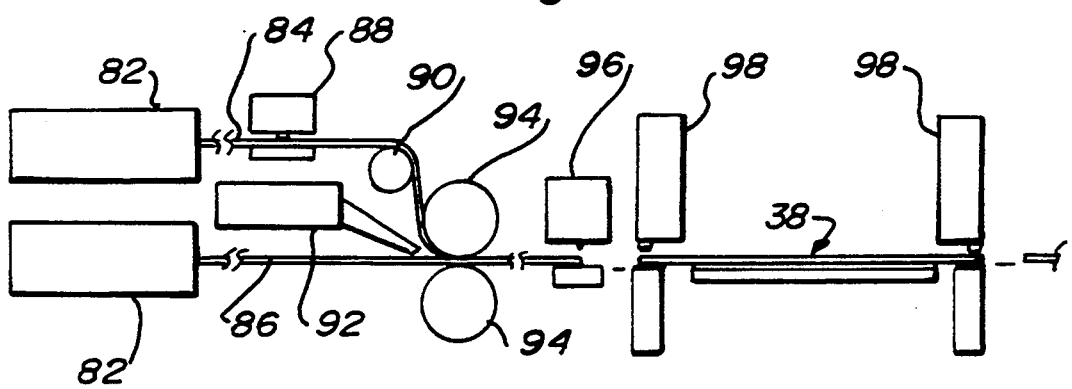
Fig_13

INFLATABLE TOURNIQUET CUFF AND METHOD OF MAKING SAME

FIELD OF THE INVENTION

The present invention relates to medical tourniquets, and more particularly to disposable inflatable tourniquet cuffs that may be wrapped around a patient's limb and inflated to provide pressure for controlling blood flow in the limb.

BACKGROUND OF THE INVENTION

Inflatable tourniquet cuffs are commonly used in the medical industry. Due to the potential for soiling the tourniquet cuff during a medical procedure, tourniquet cuffs are often discarded as medical waste following the procedure. This has led to the increased popularity of disposable inflatable tourniquet cuffs.

A typical disposable inflatable tourniquet cuff comprises an inflatable bladder contained within an outer covering. Due to the tendency of the bladder to balloon during inflation, a piece of stiffening material is typically placed between the outer covering and an outer side of the bladder opposite the patient's limb. The stiffening material prevents the cuff from ballooning outwardly or obtaining a circular cross-section and possibly rolling or becoming twisted during use.

Two examples of disposable inflatable tourniquet cuffs that utilize a stiffening member are U.S. Pat. No. 3,670,735 to Hazlewood, issued Jun. 20, 1972, and U.S. Pat. No. 4,979,953 to Spence, issued Dec. 25, 1990. Similarly, in U.S. Pat. No. 5,201,758 to Glover, issued Apr. 13, 1993, a flexible covering is attached to a stiff backing plate and an inflatable bladder is positioned therebetween.

The prior art tourniquet cuffs noted above are relatively expensive due not only to the cost of the stiffeners and the covering material, but also to the relatively complex labor intensive process required to assemble these separate components into a tourniquet cuff. Furthermore, the stiffeners and the covering material only add to an already overwhelming amount of medical waste when they are disposed along with the bladder at the conclusion of the medical treatment.

It is with regard to this background information that the improvements available from the present invention have evolved.

SUMMARY OF THE INVENTION

One of the significant aspects of the present invention relates to an inflatable cuff that may be securely yet releasably fastened about a patient. Although the inflatable cuff may find use as a blood pressure cuff or a splint for immobilizing injured limbs, it is a particular object of the present invention to provide a cuff that may be fastened about a patient's limb and inflated for use as a tourniquet.

The inflatable cuff includes an elongated inflatable bladder having an outer layer with a predetermined thickness and an inner layer with a thickness that is less than the predetermined thickness of the outer layer. A fastener system attached to the bladder releasably secures the bladder about a patient's limb so that the thin inner layer is positioned adjacent the patient's skin. Upon inflation of the bladder, the gas pressure within the bladder expands the relatively flexible thin layer to a greater degree than the thick outer layer, thereby preventing the bladder from ballooning and assuming a circular cross-section.

One preferred embodiment of the inflatable cuff includes two plastic sheets of differing thicknesses sealed together along their edges to form the inflatable bladder. Prior to sealing the two sheets, an opening is formed in the thicker sheet so that a hollow flange adapted to be connected to an inflation source may be hermetically sealed to the thicker sheet in line with the opening. The fastener system is preferably attached to the thicker sheet following the formation of the bladder. The fastener system allows the bladder to be wrapped about a patient's limb so that the thin sheet contacts the limb. When the cuff is used as a tourniquet, an inflation source connected to the flange inflates the bladder to a pressure sufficient to reduce the flow of blood within the patient's limb. The two sheets are preferably extruded from a transparent plastic so that medical personnel may view the portion of the patient's limb covered by the inflatable cuff. However, when the benefits of a transparent bladder are not required, an opaque plastic may be used to form the bladder. Additionally, a flexible padding material may be affixed to the thin sheet so that the padding contacts the patient's skin once the cuff is wrapped around the patient's limb.

Another significant aspect of the present invention relates to a method of manufacturing the inflatable cuff. The method includes extruding two separate plastic ribbons, one ribbon having a greater thickness than the other. Openings are then formed at predetermined intervals along the thicker ribbon. The thick and thin ribbons are then pressed together and sealed along their side edges. The combined ribbons are subsequently cut into predetermined lengths and sealed at their ends to form an inflatable bladder. The hollow flange is then hermetically sealed to the bladder in line with the opening and the fastener system is attached to the bladder so that the bladder may be releasably secured about a patient's limb.

Alternatively, the bladder may be extruded from a single plastic sheet having a thick wall and an opposing thin wall. The plastic sheet is cut into predetermined lengths and an opening is formed in the thick wall prior to sealing the ends of the bladder. The hollow flange and the fastener system are then attached to the bladder and, regardless of whether the plastic bladder is transparent or opaque, a flexible padding may be attached to the thin wall to enhance the comfort of the inflatable cuff.

A further significant aspect of the inflatable cuff of the present invention is the relatively small number of parts which together constitute the cuff. The lack of extraneous components such as an outer covering or a separate stiffening member substantially reduces the cost of the cuff and reduces the waste associated with the disposal of the cuff. Furthermore, the relatively simple manufacturing process further reduces the cost of the cuff, thereby enhancing the disposable nature of the cuff.

A more complete appreciation of the present invention and its scope can be obtained from understanding the accompanying drawing, which is briefly summarized below, the following detailed description of presently preferred embodiments of the invention, and the appended claims.

BRIEF DESCRIPTION OF THE DRAWINGS

FIG. 1 is an isometric view of a tourniquet cuff embodying the present invention.

FIG. 2 is an isometric view illustrating the tourniquet cuff shown in FIG. 1 wrapped about a patient's limb (shown in phantom) and connected to a pump and a pump monitor.

FIG. 3 is a section taken substantially in the plane of line 3—3 on FIG. 2.

FIG. 8 is an isometric view of a first alternative embodiment of the tourniquet cuff of the present invention.

FIG. 9 is an enlarged partial section taken substantially in the plane of line 9—9 on FIG. 8.

FIG. 10 is an isometric view of a second alternative embodiment of the tourniquet cuff of the present invention.

FIG. 11 is an enlarged section taken substantially in the plane of line 11—11 on FIG. 10.

FIG. 12 is an exploded isometric view of the components of the tourniquet cuff shown in FIGS. 1 and 2, with two sheets of an inflatable bladder shown partially delaminated for clarity.

FIG. 13 is a schematic view of a manufacturing sequence illustrating the assembly of the tourniquet cuff shown in FIGS. 1 and 2.

FIG. 14 is a schematic view of an alternate manufacturing sequence for the tourniquet cuff of the present invention.

DETAILED DESCRIPTION OF THE PREFERRED EMBODIMENTS

Figure 4:
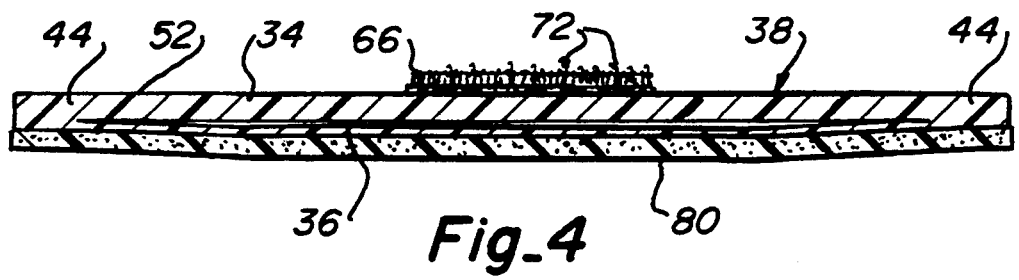
FIG. 4 is an enlarged section taken substantially in the plane of line 4—4 on FIG. 1.
Figure 5:
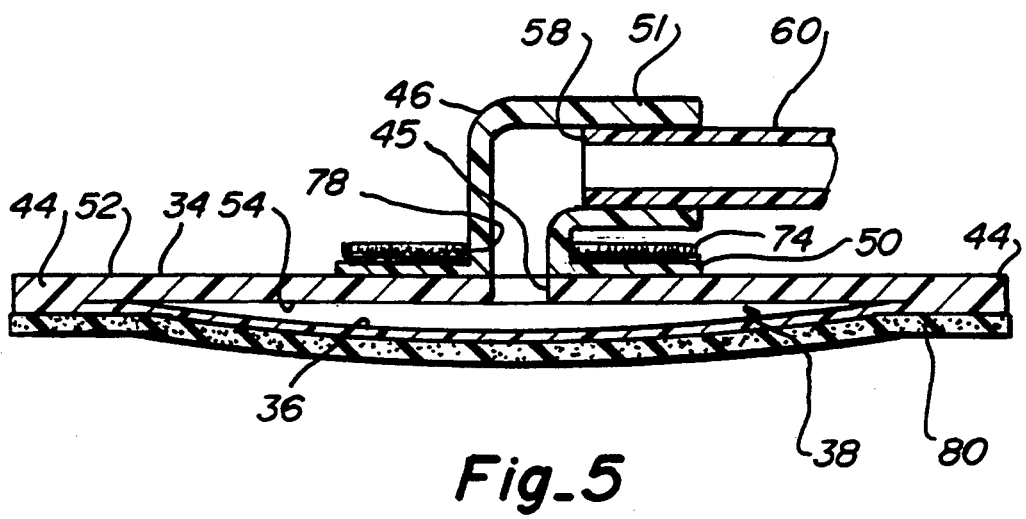
FIG. 5 is an enlarged section taken substantially in the plane of line 5—5 on FIG. 1.
Figure 6:
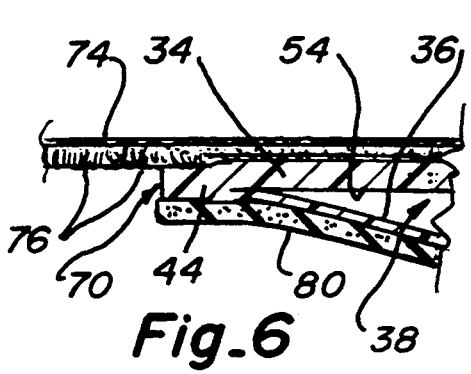
FIG. 6 is an enlarged partial section taken substantially in the plane of line 6—6 on FIG. 1.
Figure 7:
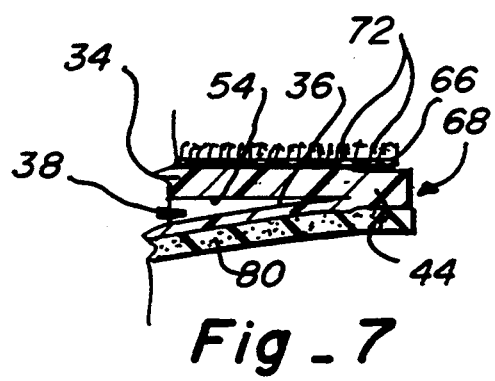
FIG. 7 is an enlarged partial section taken substantially in the plane of line 7—7 on FIG. 1.

FIG. 1 shows a disposable inflatable tourniquet cuff 20 embodying the present invention. FIG. 2 illustrates the tourniquet cuff 20 wrapped around a patient's limb 22. A single gas line on the tourniquet cuff 20 is connected to a valve 26 which, in turn, is connected by separate tubes 28 to an inflation source 30 and a gas pressure gauge 32. The inflation source 30 may comprise a conventional hand-operated air pump as shown in FIG. 2, or it may comprise an automatic tourniquet monitor that includes an air compressor. The valve 26 and gauge 32 allow medical personnel to monitor the gas pressure within the tourniquet cuff 20 in a conventional manner as the cuff is inflated.

As shown best in FIGS. 3-7 and 12, the tourniquet cuff 20 is preferably formed from a thick outer sheet or layer 34 of vinyl plastic hermetically attached to a relatively thin inner sheet or layer 36 of vinyl plastic to form an inflatable bladder 38. The outer and inner sheets 34 and 36, respectively, are preferably rectangular in shape and are hermetically sealed together along a peripheral area extending around the respective side edges 40 and 42 of the sheets 34 and 36. The seal 44 between the outer and inner sheets 34 and 36 is conventional and preferably comprises a heat seal formed by applying a hot air jet to the edges of one of the sheets and then pressing the two sheets together. Alternatively, an ultrasonic welder may be used to heat seal the sheets 34 and 36 along their edges 40 and 42. Instead of a heat seal, the seal 44 may be formed by an adhesive applied around the edge of one of the sheets prior to pressing the two sheets 34 and 36 together. In place of the adhesive, a solvent may be used to partially dissolve the vinyl along the edges 40 and 42 of both sheets 34 and 36 so that the seal 44 forms along their peripheral area as the sheets are pressed together and the vinyl is reformed.

An opening 45 is provided through the thick outer sheet 34 adjacent one end of the sheet. A hollow flange 46 having a flat first end 50 and an L-shaped neck 51 is hermetically sealed in a conventional manner to an outer surface 52 of the thick outer sheet 34 in alignment with the opening 45. Alternatively, the flat first end 50 may be sealed to an inner surface 54 of the thick outer sheet 34, prior to attaching the outer and inner sheets 34 and 36 together, so that the L-shaped neck 51 of the flange 46 extends through the opening 45. The seal between the flange 46 and the outer sheet 34 prevents gas from escaping through the opening 45 around the flange 46, thereby maintaining the integrity of the bladder 38. A first end 58 of a flexible hose 60 is hermetically sealed within the neck 51 of the flange 46, while a coupling piece 62 is attached to a second end 64 of the hose 60. The coupling piece 62 may be attached to any conventional inflation system, which might include the valve 26 shown in FIG. 2, to provide for inflation and deflation of the bladder 38.

The bladder 38 has a length dimension sufficient to extend completely around a person's limb 22. A fabric strap 66 with a length dimension that is shorter than the length of the bladder 38 is attached to the thick outer sheet 34 by conventional means (such as an adhesive or an ultrasonic weld) and extends from a first end 68 of the bladder 38 toward a second end 70, as shown in FIG. 1. The fabric strap 66 contains a multiplicity of fabric hooks 72 which face away from the thick outer sheet 34. A fabric tongue 74 having a multiplicity of fabric loops 76 along a portion of its length is attached in a conventional manner to the thick outer sheet 34 adjacent the second end 70 of the bladder 38 in longitudinal alignment with the strap 66 so that the fabric loops 76 face in an opposite direction from the fabric hooks 72. The fabric tongue 74 extends beyond the second end 70 of the bladder 38 so that its fabric loops 76 may releasably engage the fabric hooks 72 on the fabric strap 66 when the tourniquet cuff 20 is wrapped about a patient's limb 22 with the thin inner sheet 36 contacting the limb. The locking engagement of the fabric loops 76 and hooks 72 holds the tourniquet cuff 20 in position about the limb 22.

The opening 45 and the flange 46 are preferably positioned adjacent the second end 70 of the bladder 38 as shown in FIGS. 1, 2 and 12. The fabric tongue 74 preferably includes an opening 78 of sufficient size to fit over the L-shaped neck 51 of the flange 46 prior to the attachment of the hose 60 (FIG. 12). Anchoring the fabric tongue 74 about the flange 46 as shown in FIGS. 1, 2, 5 and 12 reduces the potential for accidentally pulling the fabric tongue 74 off the outer sheet 34 while tightening the tourniquet cuff 20 about a patient's limb 22.

The difference in thickness between the outer and inner sheets 34 and 36 provides the thin inner sheet 36 with a higher degree of flexibility than the thick outer sheet 34. Thus, upon inflation of the bladder 38, the relatively flexible thin inner sheet 36 expands toward and conforms to the patient's limb 22. With reference to FIG. 3, inflation of the bladder 38 causes only a slight outward expansion of the thick outer sheet 34, while the more flexible thin inner sheet 36 is expanded to a greater degree. In this manner, the thick outer sheet 34 prevents the bladder 38 from ballooning and assuming a circular cross-section which would be undesirable due to the tendency of a circular bladder to roll or become twisted.

While various thickness ratios would be suitable for the outer and inner sheets 34 and 36, the preferred embodiment of the tourniquet cuff 20 utilizes vinyl plastic extrusions wherein the outer sheet 34 is approximately four times thicker than the inner sheet 36. Specifically, the preferred embodiment utilizes an outer vinyl plastic sheet 34 and an inner vinyl plastic sheet 36 that are approximately 0.08 and 0.02 inches thick, respectively. In this manner, the inner sheet 36 is relatively elastic in comparison to the outer sheet 34 and may return to its normal size once the bladder 38 is deflated. Thus, despite the disposable nature of the cuff 20, the preferred vinyl plastic bladder 38 may allow for repeated inflation and deflation cycles.

Additionally, the outer and inner sheets 34 and 36 are preferably formed from a transparent material to allow medical personnel to view the portion of the patient's limb 22 covered by the bladder 38. An opaque rather than a transparent material may be used when the benefits of a transparent bladder are not required. While the preferred embodiment of the present invention utilizes medical grade vinyl plastic sheets, those skilled in the art will undoubtedly discern other materials that may be substituted for the vinyl plastic. However, due to discomfort that may result from pressing vinyl plastic or a similar material against a patient's skin, the tourniquet cuff 20 of the present invention may include a flexible foam padding 80 attached to the thin inner sheet 36 in a conventional manner. Thus, as shown in FIG. 3, only this relatively comfortable flexible padding 80 contacts the patient's skin once the tourniquet cuff 20 is wrapped around the patient's limb 22. However, if the foam padding 80 is not transparent it will impede or eliminate the ability to view the patient's limb 22 through the preferably transparent bladder 38 of the tourniquet cuff 20.

FIG. 13 illustrates the preferred method of manufacturing and assembling the tourniquet cuff 20 of the present invention. First, two separate extruders 82 form continuous vinyl plastic ribbons 84 and 86 of different thicknesses to form the respective outer and inner sheets 34 and 36. Next, a hole punch 88 preferably forms the openings 45 at predetermined intervals along the thicker ribbon 84. The thicker ribbon 84 is then transported by roller wheels 90 (only one of which is seen) which direct the thicker ribbon 84 toward the thinner ribbon 86. Prior to the merger of the two ribbons 84 and 86, a pair of transversely spaced nozzles 92 (only one of which is seen) preferably apply hot air jets to the side edges 42 of the thinner ribbon 86. The sides of the two ribbons 84 and 86 are then pressed together by opposing press wheels 94 to thermally seal the ribbons along their edges 40 and 42. Although hot air jets are preferably used to form the thermal seal, an ultrasonic welder may be used in place of the nozzles 92 to heat seal the two ribbons along their side edges as they are pressed together. Alternatively, a solvent or an adhesive may be applied to the edges of one of the two ribbons prior to pressing the two ribbons together.

Once the side edges of the two ribbons are sealed, a shearing machine 96 preferably cuts the combination into predetermined lengths, and the ends of the two ribbons are sealed to one another to complete the formation of the bladder 38. As shown in FIG. 13, ultrasonic welders 98 are preferably used to seal the ends 68 and 70 of the bladder 38.

Flanges 46 are then sealed to the outer surface 52 of the outer sheet 34 above and in alignment with the opening 45 (FIG. 12) in a conventional manner such as through ultrasonic welding or the application of a solvent. Next, the fabric strap 66 and tongue 74 are attached to the outer sheet 34 (FIG. 12), while the flexible padding 80 (if desired) is attached to the inner sheet 36. Finally, the hose 60 (FIG. 12) is hermetically sealed within the neck 51 of the flange 46 to complete the assembly of the tourniquet cuff 20.

Figure 15:
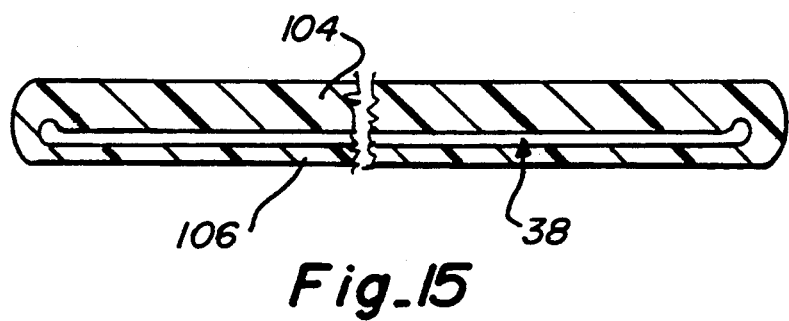
FIG. 15 is an enlarged section taken substantially in the plane of line 15—15 on FIG. 14.

FIG. 14 illustrates an alternative method of forming the bladder 38 wherein a single extruder 100 forms a vinyl plastic ribbon 102 having a thick wall 104 and a parallel opposing thin wall 106 (FIG. 15). The shearing machine 96 cuts the ribbon 102 into predetermined lengths, and a hole punch 108 then inserts an arm or mandrel (not shown) between the two walls 104 and 106 and conventionally forms the opening 45 in the thick wall 104. The ultrasonic welders 98 then seal the ends of the length of ribbon 102 to complete the formation of the bladder 38. The flange 46, fabric strap 66, fabric tongue 74 and flexible padding 80 are then attached to the bladder 38 (FIG. 12), as described above. The bladder formed in accordance with the method of FIG. 14 differs from the bladder formed in accordance with the method of FIG. 13 only in that the edges of the thick and thin walls are integrally connected (FIG. 15) rather than being hermetically connected.

A first alternative embodiment 120 of the tourniquet cuff is shown in FIGS. 8 and 9. The cuff 120 is substantially similar to the cuff 20 shown in FIGS. 1 and 2, with like reference numerals used to denote like parts such as the bladder 38. However, the cuff 120 further includes a second opening (not shown) formed in the thick outer sheet 34 and a second flange 122 hermetically sealed within the opening in fluid communication with the bladder 38 (FIG. 9). The second flange 122 is in longitudinal alignment with the first flange 46 to further anchor the fabric tongue 74 to the thick outer sheet 34. A second flexible hose 124 mated to the second flange 122 includes a second coupling piece 125 adapted for connection to a pressure gauge (not shown) which will monitor the actual flow-through gas pressure within the bladder 38 and act as a backup to the pressure gauge 32 shown in FIG. 2.

A second alternative embodiment 126 of the tourniquet cuff is shown in FIGS. 10 and 11. The cuff 126 includes the same outer and inner sheets 34 and 36 used in the first two embodiments 20 and 120 described above. However, the cuff 126 includes an additional longitudinal seal 128 between the outer and inner sheets 34 and 36 along a longitudinal centerline of the sheets to form two separate, relatively narrow inflatable bladders 130 and 130'. Like reference numbers are used to denote like parts on the tourniquet cuff 126, while a prime (') suffix is used to differentiate between the two bladders 130 and 130'. The bladders 130 and 130' each contain the single flange 46 and 46' and connecting hose 60 and 60', respectively similar to the arrangement of the tourniquet cuff 20 shown in FIGS. 1 and 2. However, both hoses 60 and 60' are connected to a single adjustable valve 132 (FIG. 10) which is capable of selectively establishing pump communication with either bladder 130 or 130', or with both bladders simultaneously. Such a dual bladder design allows medical personnel to initially inflate one of the bladders and then switch to the other bladder when the pressure exerted by the first bladder becomes irritating or painful for the patient. This procedure, known as a Bier block, is particularly useful in regional antiseptic procedures where the patient remains fully conscious.

The method of forming the tourniquet cuff 126 shown in FIGS. 10 and 11 is identical to that described above (FIG. 13) with respect to the cuff 20 shown in FIG. 1, except that the additional longitudinal seal 128 is formed along the longitudinal centerlines of the ribbons 84 and 86 (FIG. 11) at the same time the ribbons are sealed along their side edges 40 and 42. Alternatively, the bladders 130 and 130' of the cuff 126 could be formed by a single extrusion, similar to that shown in FIG. 14.

The disposable tourniquet cuffs of the present invention have several advantages over prior art disposable tourniquet cuffs. By utilizing outer and inner sheets or walls of different thicknesses, no additional stiffening member is required to control the ballooning tendency of the bladder. Additionally, no extra outer covering is required to maintain the relative positions of the bladder and the stiffening member. The omission of these extra components represents a substantial savings in both the material and the manufacturing costs involved in assembling the disposable tourniquet cuff. Additionally, the reduced number of components represents a reduction in medical waste over the prior art disposable cuffs.

Three presently preferred embodiments of the present invention have been described with a degree of particularity. These descriptions have been made by way of preferred example and are based on a present understanding of knowledge available regarding the invention. It should be understood, however, that the scope of the present invention is defined by the following claims, and not necessarily by the Detailed Description of the Preferred Embodiments.

The invention claimed is:

1. An inflatable tourniquet cuff comprising:
    an outer sheet having a predetermined thickness;
    an inner sheet attached to said outer sheet to form a first sealed bladder and a second sealed bladder between said outer and inner sheets, said first sealed bladder extending adjacent said second sealed bladder and said inner sheet having a thickness that is less than the thickness of said outer sheet;
    said first sealed bladder including a first opening through which gas may flow to inflate and deflate said first sealed bladder separately from said second sealed bladder;
    said second sealed bladder including a second opening through which gas may flow to inflate and deflate said second sealed bladder separately from said first sealed bladder; and
    means for releasably securing the first and second bladders about a patient's limb so that the inner sheet is positioned adjacent to the patient's limb.

2. An inflatable tourniquet cuff as defined in claim 1, further including a flexible pad attached to the inner sheet so that the pad contacts the patient when the first and second bladders are secured about the patient's limb.

3. An inflatable tourniquet cuff as defined in claim 1, wherein said outer and inner sheets are formed as a single plastic extrusion.

4. An inflatable tourniquet cuff as defined in claim 1, further including:
    a first connecting hose sealed within said first opening in fluid communication with said first bladder, said first connecting hose adapted to be connected to an inflation source for inflating and deflating said first bladder; and
    a second connecting hose sealed within said second opening in fluid communication with said second bladder, said second connecting hose adapted to be connected to an inflation source for inflating and deflating said second bladder.

* * * * *